(12) United States Patent
McDermott et al.

(10) Patent No.: US 9,492,252 B2
(45) Date of Patent: Nov. 15, 2016

(54) MOLDING ARTIFICIAL TEETH IN DENTURE BASE DISC

(71) Applicant: CMP INDUSTRIES LLC, Albany, NY (US)

(72) Inventors: Richard McDermott, Ballston Spa, NY (US); Devon O. Howe, Saratoga Springs, NY (US)

(73) Assignee: CMP Industries LLC, Albany, NY (US)

( * ) Notice: Subject to any disclaimer, the term of this patent is extended or adjusted under 35 U.S.C. 154(b) by 443 days.

(21) Appl. No.: 14/180,260

(22) Filed: Feb. 13, 2014

(65) Prior Publication Data

US 2014/0234802 A1  Aug. 21, 2014

Related U.S. Application Data

(60) Provisional application No. 61/765,368, filed on Feb. 15, 2013.

(51) Int. Cl.

| *A61C 13/08* | (2006.01) |
| *A61K 6/083* | (2006.01) |
| *A61C 13/00* | (2006.01) |
| *A61C 13/01* | (2006.01) |
| *A61C 13/10* | (2006.01) |

(52) U.S. Cl.
CPC .......... *A61C 13/081* (2013.01); *A61C 13/0022* (2013.01); *A61C 13/04* (2013.01); *A61C 13/10* (2013.01); *A61K 6/083* (2013.01)

(58) Field of Classification Search
CPC  A61C 13/081; A61C 13/0022; A61C 13/10; A61C 13/04; A61K 6/083
USPC ....... 264/17, 16, 18, 19, 219, 220, 221, 222, 264/223; 425/2, 175; 433/167, 202.1, 433/212.1; 249/54
See application file for complete search history.

(56) References Cited

U.S. PATENT DOCUMENTS

| 4,115,488 A | * | 9/1978 | Colpitts ................. A61C 13/04 264/17 |
| 6,488,503 B1 | | 12/2002 | Lichkus et al. |
| 8,641,938 B2 | | 2/2014 | Howe |

* cited by examiner

*Primary Examiner* — Yogendra Gupta
*Assistant Examiner* — Leith S Shafi
(74) *Attorney, Agent, or Firm* — John M. Hammond; Patent Innovations LLC (57) ABSTRACT

A method of molding artificial teeth in denture base material comprising forming a U-shaped cavity in a block of denture base material, forming socket cavities in the bottom of the U-shaped cavity, casting a fluid artificial tooth material into the cavities, and causing the fluid tooth material to solidify into solid artificial tooth material while applying pressure. Causing the solidification may include heating the fluid tooth material. The method may include casting a liquid elastomer into a bottom portion of the U-shaped cavity following forming that cavity and prior to the forming the socket cavities, curing the liquid elastomer into a solid elastomeric cushion, and removing the cushion from the U-shaped cavity. Subsequently, the cushion may be inserted into the U-shaped cavity and contacted with the fluid tooth material. A die may then be contacted with the cushion to apply pressure to it and the fluid tooth material during curing.

7 Claims, 8 Drawing Sheets

MOLDING ARTIFICIAL TEETH IN DENTURE BASE DISC

CROSS-REFERENCE TO RELATED PATENT APPLICATIONS

This application claims priority from U.S. provisional patent Application No. 61/765,368 filed Feb. 15, 2013, the disclosure of which is incorporated herein by reference.

BACKGROUND

1. Technical Field

Dental prostheses and apparatus and methods of manufacturing them. In particular, methods of molding artificial teeth in a denture base disc that may be used in computer-implemented (CAD-CAM) methods to form a removable denture. An apparatus for molding artificial teeth in a denture base disc is also disclosed.

2. Description of Related Art

According to current practice, conventional dentures are made by a dental laboratory using a "lost wax" technique. In this technique, a denture base is formed out of wax on a baseplate fitted to a stone model; then plastic denture teeth are fitted into the wax. More wax is added to form interproximal (between the teeth) contours and to make the denture appear life-like. This waxed denture (known in the industry as a "wax-up") is then delivered to a dentist for fitting into the patient's mouth. At that time, the dentist evaluates the aesthetics of the teeth of gums, and function of chewing and speech by the patient.

If adjustments are required to the wax-up, the dentist may make adjustments to the wax and/or position of the teeth, or the dentist may give instructions to the laboratory to make such adjustments. After the adjustments are made and the dentist is satisfied with the wax-up, the dental laboratory converts the wax and baseplate into a rigid methylmethacrylate plastic through a "lost wax" processing technique. This process involves the following steps:

1) A liquid slurry of a gypsum-based powder known as "dental stone" or plaster is poured into the bottom half of a metal denture flask.
2) Before the liquid dental stone begins to harden to form a solid, the lower region of the wax-up model is pushed into the liquid stone so that the liquid stone rises to the upper edge of the flask bottom half. The wax up model, which consists of the baseplate and wax denture base and the plastic denture teeth embedded in the wax base, is only immersed into the liquid stone a small distance, such that the liquid stone does not cover the teeth of the wax-up. Excess stone is removed from overflow areas on the flat edge of the flask where it will interface with an opposing flask half before the stone hardens to make it smooth and relatively flat so that no undercuts are created.
3) When the liquid dental stone hardens, its exposed top surface is coated with a separating medium such as petroleum jelly (or foil).
4) The top half of the denture flask is placed on top of the bottom half, and thus extends upwardly above the wax-up. Additional liquid dental stone slurry is poured into the top half of the flask to cover the top portion of the wax-up, including the teeth that are embedded in the wax.
5) After the dental stone has fully hardened, the flask and wax-up that is contained therein are heated to soften the wax.
6) The flask is opened, i.e., the top half and bottom half of the flask are separated. The top half of the dental flask now contains the plastic denture teeth embedded in the solid dental stone. The melted wax is washed-out with boiling water and any remaining wax is removed from the dental stone and plastic denture teeth with a brush, boiling water and soap. Sometimes, a chemical wax remover is used, followed by soap and water. Any trace of remaining wax may cause a failure of the bond between the denture teeth and the denture base. This problem is frequently the cause of denture teeth dislodging from the denture base during function (patient chewing).
7) Since the plastic denture teeth are embedded into the solid dental stone which is contained in the top half of the flask, care must be maintained not to dislodge the teeth from the stone. In order to enhance the bond between the plastic teeth and the denture base that will subsequently be formed and bonded to them, a dental laboratory technician will sometimes lightly grind the exposed surfaces of the teeth that were embedded in the wax in order to break the shiny surface (glaze) on the surfaces. In some cases, a technician will also drill very small holes into the exposed teeth bottoms (sometimes called "diatorics") in order to allow denture base material to flow into the holes, thereby improving mechanical retention. However, the use of diatorics is risky because they often are the cause of denture tooth fracture.
8) The denture base material is then prepared and contacted with the teeth to form the denture. The most common type of denture base material used in the United States is a heat-cured methylmethacrylate material. Methylmethacrylate powder and a suitable liquid are mixed together to form a dough. The dough is placed in the void volumes of the top half of the flask which contain the artificial teeth. The void volume in the top half of the flask previously contained a portion of the wax, which was removed as described above; this top void volume now forms a mold of the upper portion of the denture base, into which the bottoms of the teeth embedded in the dental stone extend. In like manner, the void volume in the bottom half of the flask also previously contained a portion of the wax, which was removed as described above; this bottom void volume now forms a mold of the lower portion of the denture base. After placing a thin sheet of polyethylene on the bottom half, the top and bottom halves of the flask are placed together, forming a complete mold of the denture base with the dough contained therein. The flask is then placed in a press at approximately 1,000 psi to compress the dough, thereby squeezing the dough and causing it to flow into the voids that were once wax.
9) Because methylmethacrylate polymers shrink when they polymerize, it is common practice to "trial pack" the denture several times. "Trial packing" means that the denture base dough is placed in the flask and pressed, then the flask is opened again and more dough is added, then closed and pressed again. This process is repeated until the operator subjectively determines that the denture base is packed as tightly as possible. Before the last packing is done, the thin polyethylene sheet is removed from the bottom half. The last "trial pack" is typically performed at about 3,000 psi.
10) The flask then is inserted into hot water to start the polymerization process. Most heat-cured methylmethacrylate polymers are cured at about 165° F. for a few hours; then the water temperature is increased to boiling (approximately 212° F.) for at least 30 minutes. The purpose of the lower temperature cycle is to initiate polymerization. If the temperature is initially too hot, the polymer will cure too quickly, causing porosity in the denture base. The porosity is caused by rapid curing and shrinkage of the polymer before uncured polymer can fill the shrinking area. The purpose of raising the temperature at the end of the cycle is to complete the polymerization process as much as possible.

11) The last steps are to remove the denture from the flask by opening the two flask halves; then use plaster nippers or an air chisel to remove stone from the denture (devesting); then the denture base is adjusted with a high-speed bur and polished with a rag wheel and abrasives and/or polishing media.

There are many problems with this conventional denture base fabrication method and related materials and systems:

1) Due to the many steps of processing a denture as summarized above, there are chances of introducing an error into the steps, thereby potentially increasing fit problems.

2) Tooth de-bonding from the denture base is a common problem. This is often caused by the presence of traces of remaining wax on the bottoms of the teeth, which cause a failure of the bond between the denture teeth and the denture base. Tooth fracture is also a common problem, particularly when diatorics are used in an attempt to strengthen the bond of the teeth to the denture base as described above.

3) Human errors cause inconsistencies in the denture fabrication process, which can result in defects and failures as described above, and/or poor denture fit. Examples of human errors are using different ratios of methylmethacrylate powder/liquid, using different flask closure pressures, water levels, or temperatures that vary from fabrication to fabrication. Inconsistencies can also be caused by environmental variation, such as differences in ambient temperature and/or humidity. Underpacking is an error caused by not using enough dough or too little clamping pressure. This can result in porosity (small bubbles) that may weaken the denture and make it prone to bacteria growth. Overpacking occurs when too much dough is used and then the flask halves don't fully close together and have intimate contact. This can result in mal-fitting dentures or "open bites" as is referred to by dentists. Another introduction of potential for human error is the finishing step. In the process of removing imperfections in a denture that has been devested, some dental technicians may over adjust (remove excessive denture base material), resulting in denture base that is too thin and prone to breakage. Also, the polishing step—which is the process to remove scratches created in the finishing step—a dental technician may over-polish the denture teeth, which can remove intended delicate imperfections in the artificial teeth or anatomy that may alter the esthetics and/or function of the artificial teeth.

4) Denture base material shrinkage causes internal stresses which are a source of denture fit problems. During the denture base forming part of the process, methylmethacrylate denture base material polymerizes and shrinks rapidly at first, causing internal stress in the denture base, especially in areas of differing thicknesses. After a denture in devested (removed from denture flask), this internal stress may cause dimensional distortion. Although some commercial continuous pressure curing systems (such as the Ivocap® system by Ivoclar Vivodent, Inc., or the Success® Injection System by Dentsply Prosthetics) reduce this stress, methylmethacrylate continues to slowly polymerize over time until residual monomers are virtually eliminated. Thus distortion (resulting in poor fit) can occur after a denture is completed by a dental laboratory and shipped to a dentist.

Figure 8:
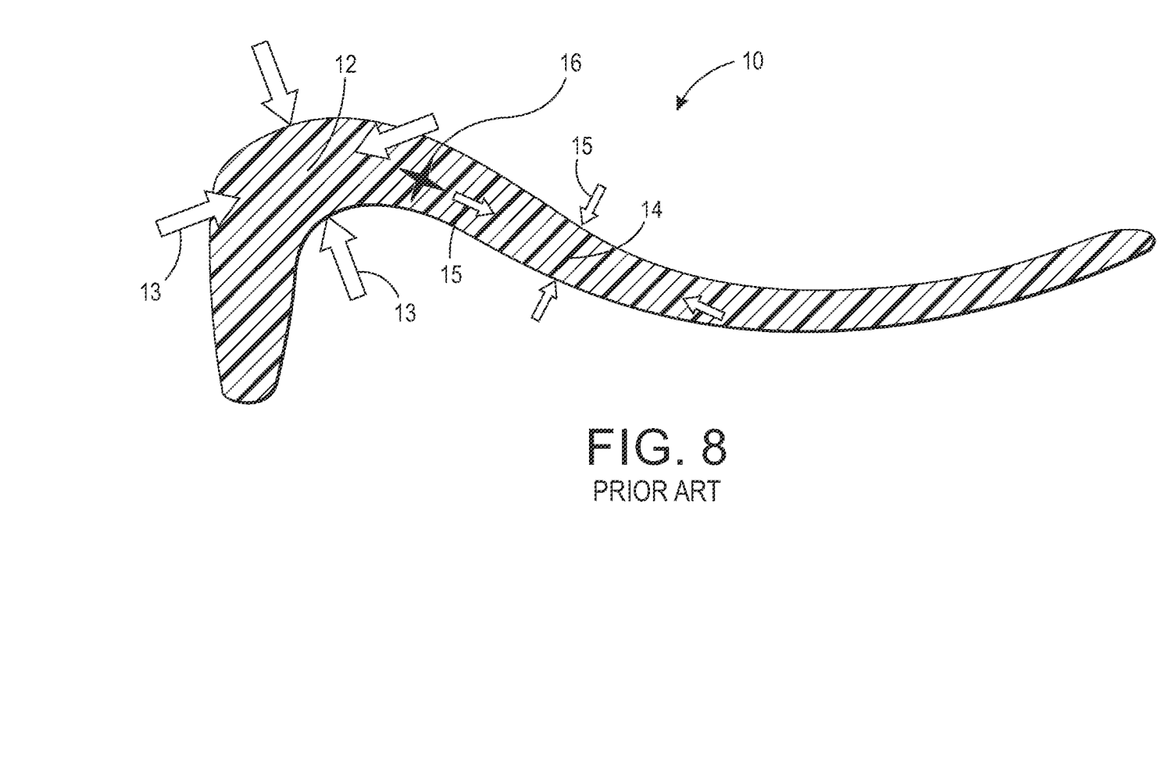
FIG. 8 is a side cross-sectional view of a portion of a denture made according to prior art methods, the view showing non-uniform shrinkage and stresses in the denture. The larger arrows are shown to represent thicker areas, which are prone to more shrinkage than thinner areas, which are represented by smaller arrows.

This last problem is illustrated in FIG. 8, which shows a cross-section of a denture base 10 taken along the midline thereof. It can be seen that the denture base 10 has regions of different thickness which may result in areas of more shrinkage than other areas during polymerization of the methylmethacrylate. For example, the thicker region 12 may undergo a greater degree of shrinkage (as indicated by large arrows 13), that the shrinkage of the thinner region 14 (as indicated by smaller arrows 15. These areas of shrinkage differential create stress points, such as stress point 16. Such stress points may cause dimensional distortion of the denture base, resulting in the denture having a poor fit to the patient's mucosa.

The dental laboratory industry in the United States is currently undergoing some changes away from "lost-wax" techniques to computer-aided-design (CAD) and computer-aided-manufacturing (CAM) of dental products. Dental crowns and bridges have been milled using CAD-CAM technologies for many years. The use of these technologies for crowns and bridges has been increasing rapidly in recent years. However, there has been very little use of CAD-CAM technologies in the area of removable prosthodontics (e.g., dentures, partials, etc.).

There are several reasons why CAD-CAM has not been more widely used in removable prosthodontics. A major reason is that satisfactory software for occlusion (i.e., mapping of how upper and lower teeth work together) has not been developed. Another reason is because a denture is made from two colors of materials (a pink base and white teeth), and dental milling systems are based on monolithic materials. Additional reasons are described in the Applicant's commonly owned U.S. Pat. No. 8,641,938 of Howe for a "Denture and Method and Apparatus of Making Same," the disclosure of which is incorporated herein by reference.

What is needed is a simple, low cost method of manufacturing a denture in which the denture is accurately formed, dimensionally stable, and robust, i.e., resistant to loosening and/or loss and/or fracture of teeth.

SUMMARY

In accordance with the present disclosure, methods and apparatus are provided which meet the above need.

In one broad aspect of the present disclosure, a method is provided for molding artificial denture teeth in a denture base disc that is used in a CAD-CAM milling technique to form a removable denture. In accordance with the invention, a pre-cured denture base disc is used. The disc has a "U" shaped trough formed therein or the "U" shaped trough can be formed by a milling machine. A milling machine is used to cut sockets where artificial teeth will be molded. After pouring a fluid artificial tooth material, such as methylmethacrylate, into the voids or sockets created by the milling machine, an elastomeric pressure transfer cushion is placed over the uncured artificial tooth material. Then a "U" shaped die is placed on top of the elastomeric transfer cushion. Then the assembly is placed in a press, and the fluid artificial tooth material is cured into solid artificial tooth material. Following the curing to form solid artificial tooth material embedded in the block of denture base material, the block is removed from the press. A removable denture may then be made by using a CAD-CAM operated mill to remove portions of the denture base material and portions of the artificial tooth material, the denture comprised of a plurality of artificial teeth joined to the denture base.

In another aspect of the present disclosure, the method described above for molding artificial denture teeth in a denture base disc solves a problem with using rigid materials for the die—such as metals—to press the fluid artificial tooth material into the denture base disc. The problem is that the uncured artificial tooth material shrinks substantially during the curing process, and solid die materials cannot apply uniform pressure throughout the shrinkage process, especially if curing and shrinkage first occurs in close proximity to the surface of the die. For example, the artificial tooth material methylmethacrylate shrinks from 6 to 11 percent during the curing process.

When using solid material dies to apply pressure to the artificial tooth material, porosity (i.e., small voids) may form in the methylmethacrylate material as it shrinks. This is because some parts of the methylmethacrylate polymerize to form solid regions, and prohibit the die from compressing other areas of methylmethacrylate that are not yet polymerized and are continuing to shrink as they polymerize. In contrast, using the elastomeric pressure transfer cushion to apply pressure to the artificial tooth material keeps all of the material under pressure until it is fully polymerized, thereby solving the problem of formation of small voids in the material when it is cured using a rigid material to apply pressure.

In another aspect of the present disclosure, there is provided a method of molding artificial teeth in a denture base material. The method comprises forming a first cavity in a block of a denture base material, the first cavity having a bottom wall and a side wall and formed to correspond to the U-shaped contour of natural teeth as arranged on maxillae or on a mandible; forming a plurality of socket cavities in the block of denture base material, the socket cavities extending downwardly from the bottom wall of the first cavity into the denture base material; casting a first fluid artificial tooth material into the plurality of socket cavities and into a portion of the first cavity, thereby filling the socket cavities and forming a top fluid surface in the first cavity; applying pressure to the first fluid artificial tooth material contained in the portion of the first cavity and the socket cavities; and causing the first fluid artificial tooth material to solidify into a first solid artificial tooth material while applying pressure to the first fluid artificial tooth material.

Causing the first fluid artificial tooth material to solidify into a first solid artificial tooth material may include heating the first fluid artificial tooth material. The heating may be accomplished by heating the bottom of the block of denture base material, and causing heat transfer from the bottom of the block of denture base material into the first fluid artificial tooth material.

The method may include casting a liquid elastomer into a first bottom portion of the first cavity following the forming the first cavity in the block of a denture base material and prior to the forming the plurality of socket cavities, curing the liquid elastomer into a solid U-shaped elastomeric cushion, and removing the cushion from the first cavity. Subsequently, the U-shaped elastomeric cushion may be inserted into the first cavity after casting the first fluid artificial tooth material, and contacting the cushion with the top fluid surface of the first fluid artificial tooth material. A pressure element may then be contacted with the U-shaped elastomeric cushion so as to apply pressure to the cushion. The cushion thus functions as the source of pressure on the first fluid artificial tooth material contained in the second bottom portion of the first cavity and the socket cavities. The first fluid artificial tooth material is solidified into the first solid artificial tooth material while under pressure as described above.

With denture teeth having been thusly molded in a denture base material, there is further provided a method for making a denture comprised of a base and a plurality of teeth joined to the base. The method is comprised of removing a portion of the first solid artificial tooth material to form the plurality of teeth, and removing a portion of the block of denture base material to form the denture base.

In another aspect of the present disclosure, there is provided an apparatus for forming artificial teeth in a denture base material. The apparatus comprises a material removal device, a liquid elastomer source, a first fluid artificial tooth material source, and a pressure element. The material removal device is operable to first form a first cavity in a block of a denture base material. The first cavity has a bottom wall and a side wall and formed to correspond to the U-shaped contour of natural teeth as arranged on maxillae or on a mandible. The material removal device is also operable to subsequently form a plurality of socket cavities in the block of denture base material, which extending downwardly from the bottom wall of the first cavity into the denture base material. The liquid elastomer source is operable to deliver a liquid elastomer into the first cavity. The first fluid artificial tooth material source is operable to deliver a first fluid artificial tooth material into the first cavity. The pressure element is configured to apply pressure to a top surface of first fluid artificial tooth material disposed in the first cavity. The apparatus may include a heater in thermal communication with a bottom of the block of denture base material.

The apparatus may be further comprised of a solid elastomeric cushion. The cushion may be formed by casting a liquid elastomer into a first bottom portion of the first cavity following the forming the first cavity in the block of denture base material and prior to the forming the plurality of socket cavities, curing the liquid elastomer into a solid U-shaped elastomeric cushion, and removing the cushion from the first cavity. The elastomeric cushion is disposable in the first cavity between the top surface of first fluid artificial tooth material disposed in the first cavity and the pressure element.

BRIEF DESCRIPTION OF THE DRAWINGS

The present disclosure will be provided with reference to the following drawings, in which like numerals refer to like elements, and in which.

The present invention will be described in connection with certain preferred embodiments. However, it is to be understood that there is no intent to limit the invention to the embodiments described. On the contrary, the intent is to cover all alternatives, modifications, and equivalents as may be included within the spirit and scope of the invention as defined by the appended claims.

DETAILED DESCRIPTION

For a general understanding of the present invention, reference is made to the drawings. In the drawings, like reference numerals have been used throughout to designate identical elements.

Figure 1:
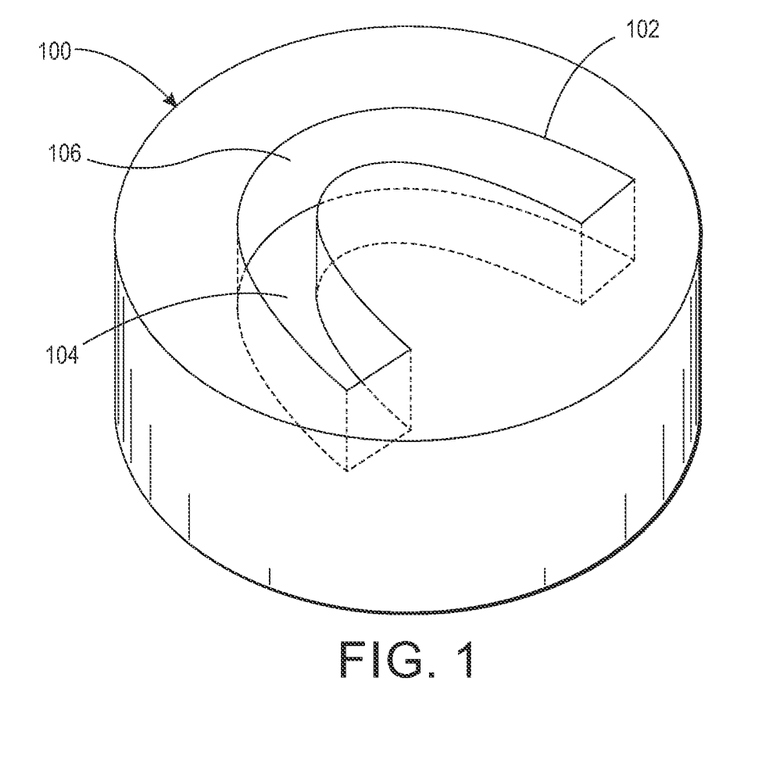
FIG. 1 is a perspective view of a block of denture base material having a U-shaped cavity formed therein according to a method of the present disclosure.

The Applicant's method and apparatus for molding artificial teeth in a denture base material will now be described with reference to FIGS. 1-7. Turning first to FIG. 1, the instant method comprises forming a first cavity 102 in a block 100 of a denture base material. The first cavity 102 has a bottom wall 104 and a side wall 106. The first cavity is formed to correspond to the U-shaped contour of natural teeth as arranged on maxillae or on a mandible. The first cavity is formed by an apparatus that includes a material removal device (not shown). In certain embodiments, the material removal device may be a mill. The mill may be a mill as disclosed in the aforementioned U.S. Pat. No. 8,641,938 of Howe. In certain embodiments, the width of the U-shaped cavity 102 may be about 0.5 inches wide, and the depth may be about 0.5 inches deep.

Figure 2:
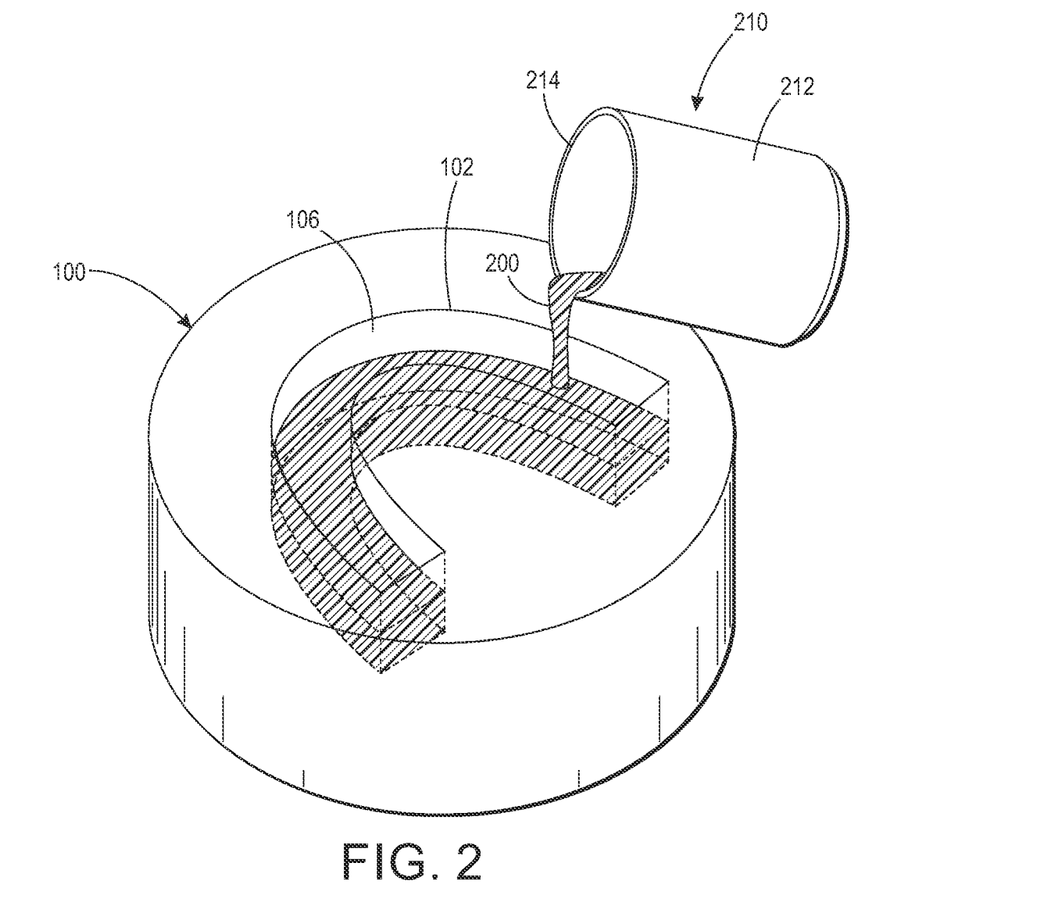
FIG. 2 is a perspective view of an elastomeric cushion in the process of being formed according to a method of the present disclosure.

The method may include casting a liquid elastomer into a bottom portion of the U-shaped cavity 102, curing the liquid elastomer into a solid U-shaped elastomeric cushion, and removing the cushion from the U-shaped cavity. Referring to FIG. 2, the apparatus for forming artificial teeth in the denture base material may include a liquid elastomer source 210. In the embodiment depicted in FIG. 2, the source 210 may be comprised of a can 212 having an open top 214 from which the liquid elastomer 200 is poured into the U-shaped cavity 102. In embodiments (not shown) that are more amenable to automation, the source 210 may be comprised of a syringe containing the liquid elastomer (similar to syringes disclosed in U.S. Pat. No. 8,641,938), or another vessel and delivery means such as a pump.

Figure 3:
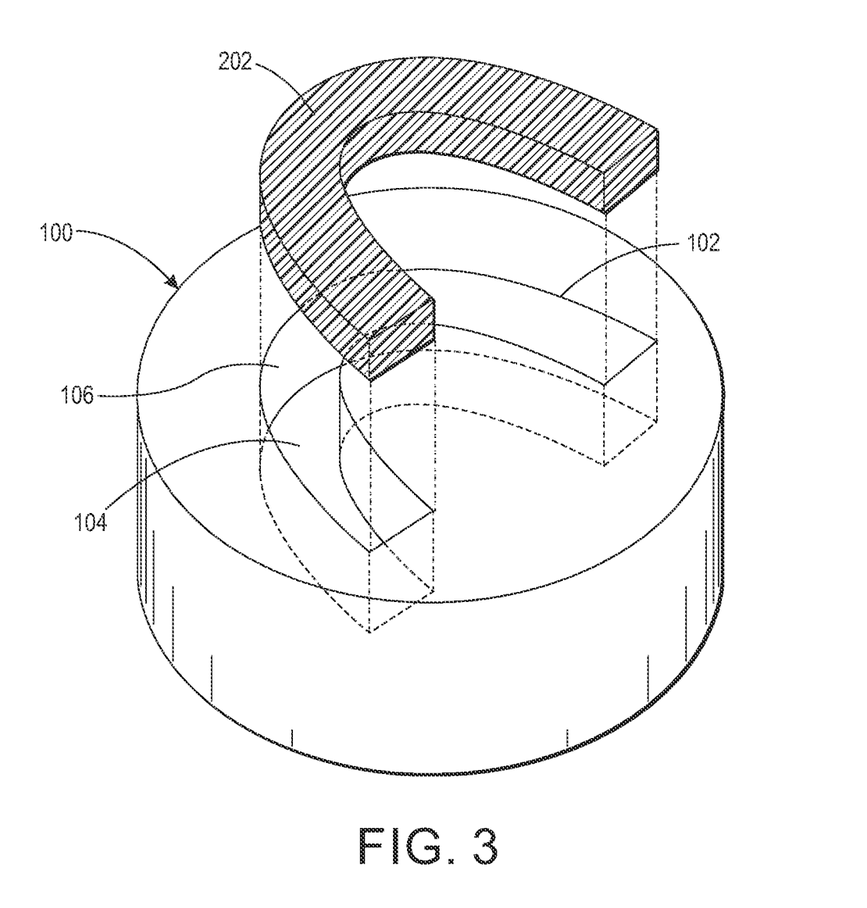
FIG. 3 is a perspective view of the elastomeric cushion after completion of formation and removal from the U-shaped cavity in the block of denture base material.

After the delivery of liquid elastomer 200 into the cavity 102 is completed, the elastomer levels to a uniform liquid thickness, and is cured into a solid U-shaped elastomeric cushion 202. In certain embodiments, the liquid elastomer 200 may be a liquid silicone elastomer, which is cured into a solid silicone elastomer. The minimum thickness of the liquid elastomer 200 in the cavity may be between 0.2 and 0.4 millimeters thick. Minimal shrinkage occurs during curing, and thus the minimum thickness of the cured solid elastomeric cushion 202 may also be between 0.2 and 0.4 millimeters thick. While the cured solid elastomeric cushion 202 may be much thicker, one that is significantly thicker will reduce the space available in a press to be used later in the process, as will be described subsequently herein. Referring to FIG. 3, after the liquid elastomer 200 is cured to form a solid elastomer, the solid elastomeric cushion 202 is removed from the U-shaped cavity 102 of the block 100 of denture base material. Thus the U-shaped cavity 102, which will be used for other purposes to be described subsequently herein, is first used as a mold to make a U-shaped elastomeric cushion that precisely dimensionally matches the U-shaped cavity 102, and that will also be used as described subsequently herein.

Figure 4:
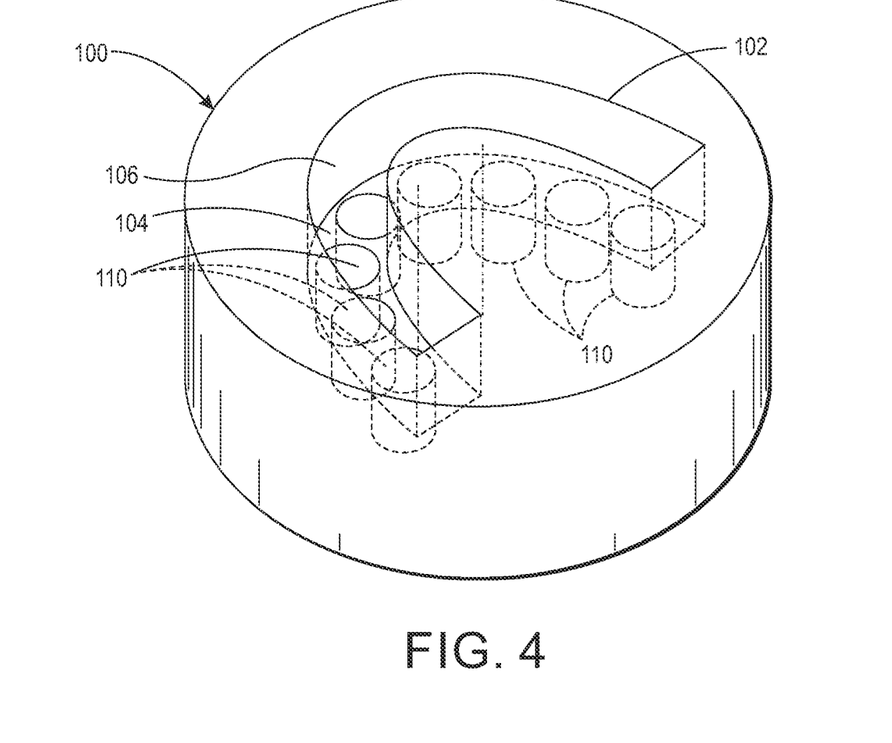
FIG. 4 is a perspective view of the block of denture base material after formation of socket cavities extending downwardly from the bottom of the U-shaped cavity formed in the block.

Referring to FIG. 4, the method further comprises forming a plurality of socket cavities 110 in the block 100 of denture base material. The socket cavities 110 may be formed with a mill (not shown). The socket cavities 110 extend downwardly from the bottom wall 104 of the U-shaped cavity 102 into the denture base material. Although the socket cavities 110 are shown in FIG. 4 as being of a uniform size and in a uniform arrangement, it is to be understood that the number of cavities 110 and their sizes and locations may be selected to correspond to the number and sizes and locations of artificial teeth to be formed in the denture base material. The socket cavities 110 provide a more extensive interface between the denture base material and the molded teeth than would otherwise be present if they were not provided, and thus serve to form a stronger bond between the denture base material and molded teeth.

Figure 5:
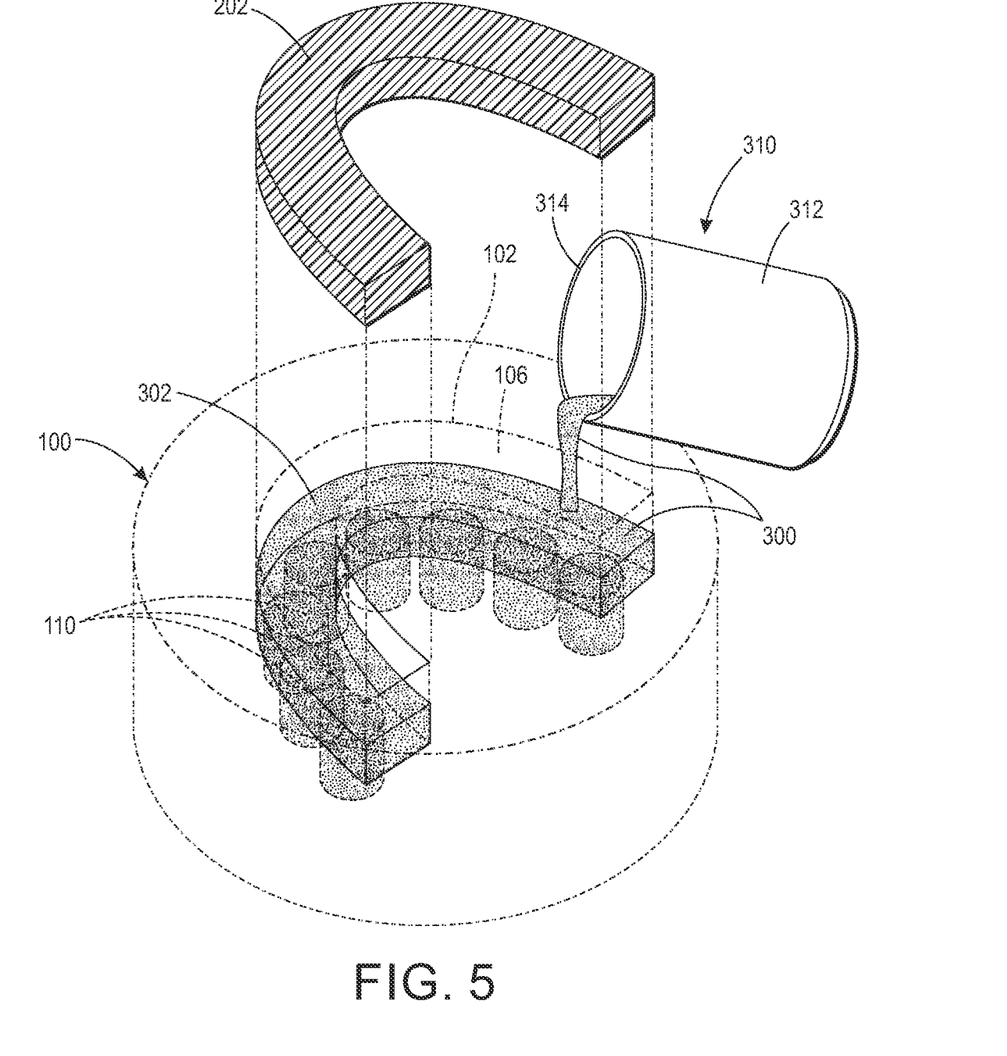
FIG. 5 is a perspective view of the casting a first fluid artificial tooth material into the plurality of socket cavities and into a portion of the first cavity formed in the block.

The method further comprises casting a fluid artificial tooth material—as described in U.S. Pat. No. 6,488,503 Lichkus, et. al. for a "Prosthetic teeth and method of making therefor,"—into the plurality of socket cavities 110 and into the bottom portion of the U-shaped cavity 102, thereby filling the socket cavities 110 and forming a top fluid surface in the U-shaped cavity 102. The disclosure of U.S. Pat. No. 6,488,503 is incorporated herein by reference. Referring to FIG. 5, the apparatus may include a fluid artificial tooth material source 310. In the embodiment depicted in FIG. 5, the source 310 may be comprised of a can 312 having an open top 314 from which the fluid artificial tooth material 300 is poured into the U-shaped cavity 102 and into the sockets 110 extending downwardly therefrom. In embodiments (not shown) that are more amenable to automation, the source 310 may be comprised of a syringe or a pump and vessel as described previously for delivery of the liquid elastomer 200 (FIG. 2).

In certain embodiments, the fluid artificial tooth material 300 may be comprised of methylmethacrylate. The fluid artificial tooth material 300 may be formulated from tooth-colored high density methylmethacrylate polymers and monomers. The fluid artificial tooth material 300 may be formulated as a slurry of methylmethacrylate powder that is dispersed in a suitable carrier liquid. Suitable carrier liquids include liquid monomers such as the methylmethacrylate monomer, and ethyl methacrylate monomer. The monomers are capable of saturating and swelling the methylmethacrylate polymer powder. The fluid artificial tooth material 300 is preferably formulated in a controlled environment with ambient conditions of between 60° F. to 80° F. at a relative humidity between 50% to 70%. Consistent ratios of powder and liquid are used so that properties such as viscosity, solids loading, and curing reaction rates of the fluid artificial tooth material 300 are reproducible from batch-to-batch.

In addition, it is preferred that the mixture must undergo an aging or "bench set" time, in order for the liquid to be absorbed and swell the powder. If too little time is allowed for "bench set," the liquid may not be fully absorbed by the powder. In such circumstances, the liquid will squeeze out during compression (as described subsequently herein); thus the ratio of the mixture remaining in the press will be dryer than normal which will affect physical properties of the cured artificial tooth material polymer. Additionally, if too much time is allowed for "bench set," the mixture may become stiff and thus be difficult to pour and may trap air in undercut areas of the milled denture base. The optimum "bench set" time depends on the artificial tooth material polymer used. In experimental trials using polymethylmethacrylate powder, 6-8 minutes was found to be optimal, while at 12 minutes, the mixture undesirably started to thicken as described above.

By formulating the artificial tooth material 300 using consistent ratios of powder and liquid, ambient environmental conditions, and "bench set" times, the properties of the resulting solid artificial tooth material are also maintained consistent from denture to denture.

Figure 6:
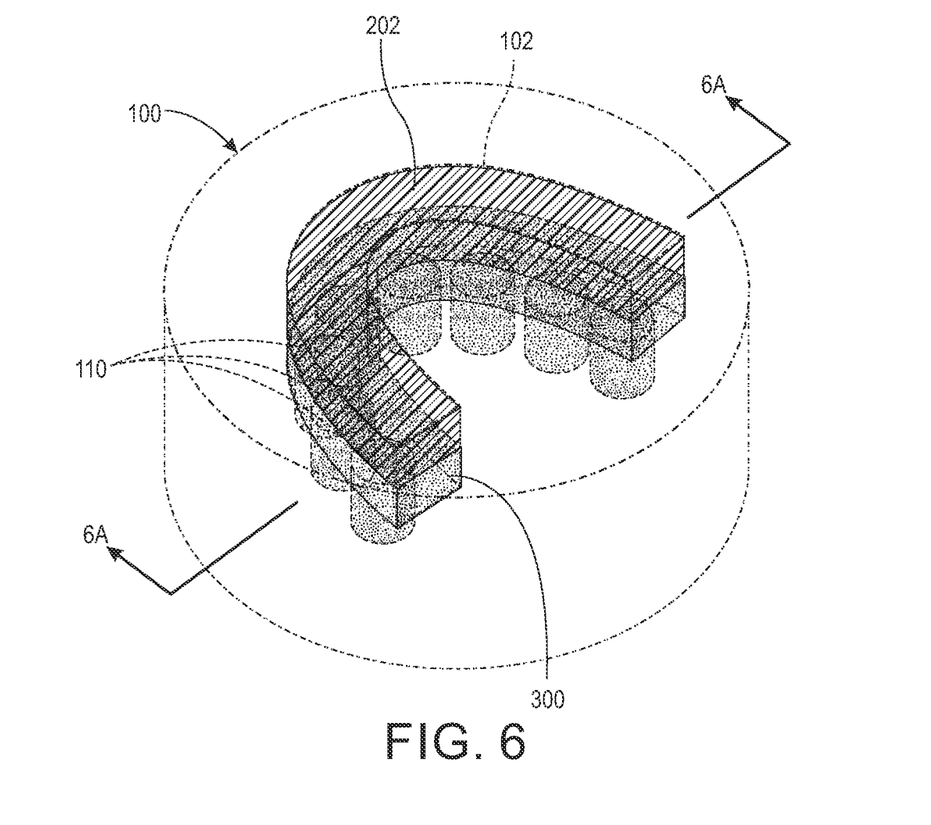
FIG. 6 is a perspective view of the contacting of the elastomeric cushion with the top fluid surface of the first fluid artificial tooth material disposed in the plurality of socket cavities and in the first cavity.
Figure 6A:
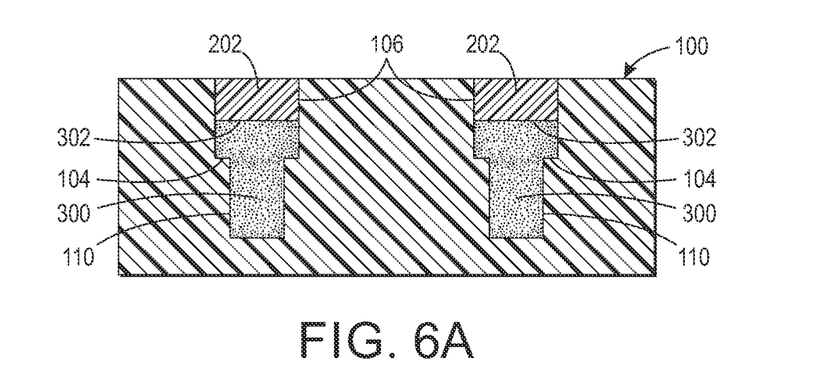
FIG. 6A is a side cross-sectional view of the contacting of the elastomeric cushion with the top fluid surface of the first fluid artificial tooth material disposed in the plurality of socket cavities and in the first cavity, taken along line 6A-6A of FIG. 6.

The method further comprises applying pressure to the fluid artificial tooth material 300 contained in the portion of the first cavity 102 and the socket cavities 110, and causing the fluid artificial tooth material 300 to solidify into a solid artificial tooth material while applying pressure to the fluid artificial tooth material 300. Referring to FIGS. 5, 6, and 6A, the apparatus for forming artificial teeth in a denture base material may include the U-shaped elastomeric cushion 202. After the fluid artificial tooth material 300 has been cast in the U-shaped cavity 102 and the socket cavities 110, the U-shaped elastomeric cushion 202 may be inserted into the U-shaped cavity 102. The elastomeric cushion 202 is contacted with the top fluid surface 302 of the fluid artificial tooth material 300.

Figure 7:
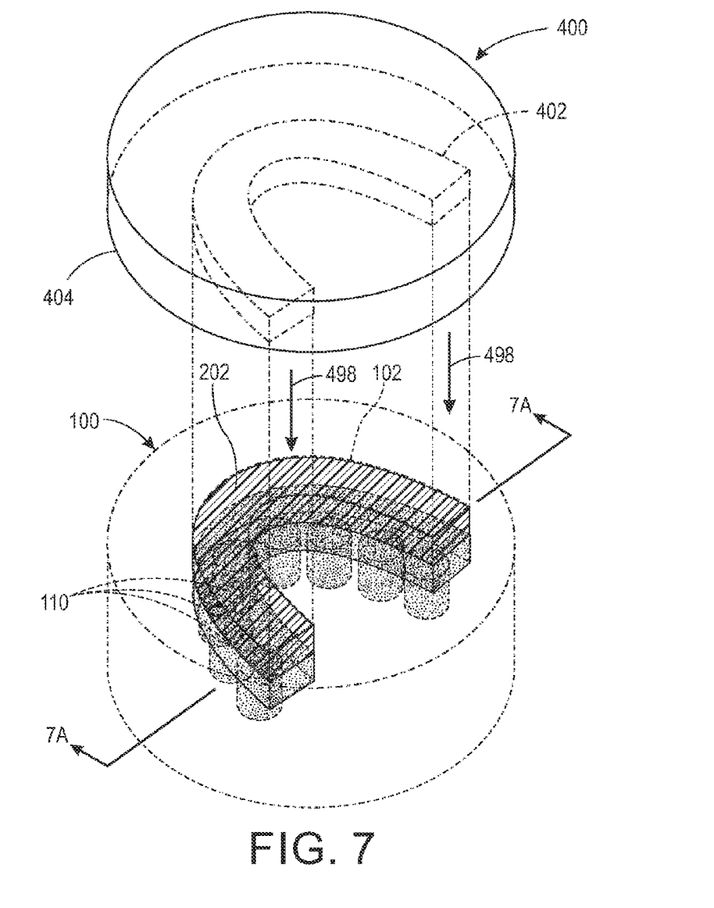
FIG. 7 is a perspective view of the application of pressure on the elastomeric cushion and on the top fluid surface of the first fluid artificial tooth material by forcing a pressure element downwardly against the elastomeric cushion.
Figure 7A:
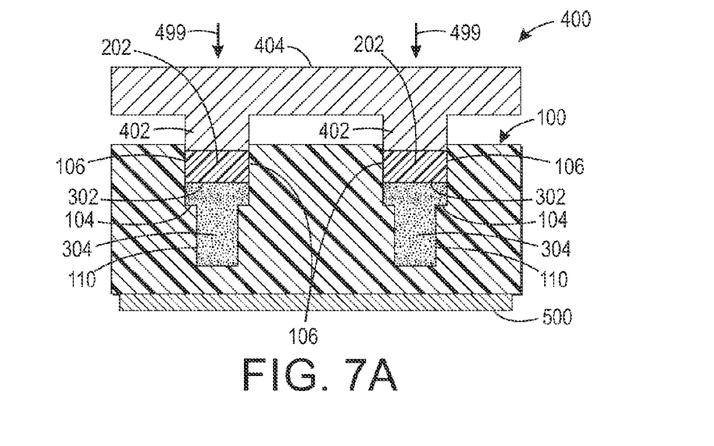
FIG. 7A is a side cross-sectional view of the application of pressure on the elastomeric cushion and on the top fluid surface of the first fluid artificial tooth material during curing of the fluid artificial tooth material into solid artificial tooth material.

Referring to FIGS. 7 and 7A, a pressure element 400 may then be contacted with the U-shaped elastomeric cushion 300 as indicated by arrows 498 so as to apply pressure to the cushion 202. The pressure element 400 may be comprised of a U-shaped die 402, which is joined to or formed integrally with a pressure plate 404.

Referring to FIG. 7A, the fluid artificial tooth material 300 is caused to solidify into a solid artificial tooth material 304 while applying pressure to the fluid artificial tooth material 300. The block 100 of denture base material may be placed in a press (not shown), with the U-shaped die 402 in contiguous contact with the U-shaped elastomeric cushion 202. The U-shaped die 402 has a shape corresponding to the shape of the U-shaped elastomeric cushion 202, but with a perimeter that is slightly smaller than the outer perimeter of the U-shaped elastomeric cushion 202, and slightly smaller than the dimensions of the side wall 106 of the U-shaped cavity 102. In that manner, when force is applied by the press (not shown) to the pressure plate 404 as indicated by arrows 499, the U-shaped die 402 can extend downwardly into the U-shaped cavity 102 as the fluid artificial tooth material 300 cures (with some shrinkage) to form solid artificial tooth material 304 in the socket cavities 110 and the lower portion of U-shaped cavity 102.

In an alternative embodiment, the U-shaped die 402 of the pressure element 400 may be contacted directly with the upper surface 302 of the fluid artificial tooth material 300, and apply pressure to the surface 302 during curing to form solid artificial tooth material. However, this is a less preferred method of molding artificial teeth in the denture base material, because a problem may occur when using rigid materials, such as a metal, for the die 402 to press the fluid artificial tooth material 300 into the socket cavities 110 and the lower portion of U-shaped cavity 102 of the block 100 of denture base material. The problem is that the uncured fluid artificial tooth material 300 shrinks substantially during the curing process, and solid die materials cannot apply uniform pressure throughout the shrinkage process. For example, the artificial tooth material methylmethacrylate shrinks from 6 to 11 percent during the curing process.

Thus when using a solid material die to apply pressure to the fluid artificial tooth material 300, porosity (i.e., small voids) forms in the artificial tooth material as it shrinks. This is because some parts of the artificial tooth material, such as polymethylmethacrylate, polymerize to form solid regions, and prohibit the die from compressing other areas of artificial tooth material that are not yet polymerized and are continuing to shrink as they polymerize. In contrast, and advantageously, using the elastomeric pressure transfer cushion 202 to apply pressure to the fluid artificial tooth material 300 keeps all of the material under pressure until it is fully polymerized into solid artificial tooth material 304, thereby solving the problem of formation of small voids in the material 304 when it is cured by only using a rigid material to apply pressure. Additionally, the U-shaped elastomeric cushion 202 is made of an elastomer material, such as silicone, that does not adhere to the solid artificial tooth material 304. In that manner, the cushion 202 can easily be removed from the U-shaped cavity 102 after the curing process is complete.

In certain embodiments, causing the fluid artificial tooth material to solidify into a solid artificial tooth material may include heating the fluid artificial tooth material. Referring to FIG. 7A, the heating may be accomplished by a heater 500 that is in thermal communication with the bottom of the block 100 of denture base material. Accordingly, heat transfer is caused from the bottom of the block 100 of denture base material into the fluid artificial tooth material 300. In certain embodiments, the heater 500 is controlled such that the temperature of the heating unit is about 250° F. to 280° F. In experimental trials, the Applicant has observed that temperatures below 250° F. resulted in artificial tooth material 300 that was not completely polymerized, while temperatures above 280° F. resulted in discoloration of the block 100 of denture base material. Heat is preferably applied to the bottom of the block 100 so that curing begins at the bottom and proceeds toward the pressure created by the bottom surface of the die 402. If the sides of the block 100 are heated, the tooth material may fracture in the middle from being stretched from each side as the material shrinks. The press (not shown) is activated to preferably provide at least 1500 pounds per square inch of pressure on the bottom surface of the die 402. The use of less pressure may result in porosity. The pressure and temperature are maintained for 15 minutes to cause the curing from fluid to solid tooth material 304.

Following the curing to form solid artificial tooth material 304 embedded in the block 100 of denture base material, the block 100 is removed from the press. A heat-treatment process can be performed to further polymerize the solid artificial tooth material 304 embedded in the block 100 of denture base material. This heat-treatment process will relieve most residual stresses in both the solid artificial tooth material 304 and the block 100 of denture base material so that the materials are near fully polymerized and as a result, will be more dimensionally stable. A removable denture (not shown) may then be made by using a CAD-CAM operated mill (not shown) to remove portions of the denture base material and portions of the artificial tooth material. The denture is comprised of a plurality of artificial teeth joined to the denture base. The denture may be made by milling according to the methods disclosed in the aforementioned U.S. Pat. No. 8,641,938 of Howe.

It is, therefore, apparent that there has been provided, in accordance with the present invention, a method and apparatus for molding artificial teeth in a denture base disc. Having thus described the basic concept of the invention, it will be rather apparent to those skilled in the art that the foregoing detailed disclosure is intended to be presented by way of example only, and is not limiting. Various alterations, improvements, and modifications will occur to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims.

We claim:

1. A method of molding artificial teeth in a denture base material, the method comprising:
   a) forming a first cavity in a block of a denture base material, the first cavity having a bottom wall and a side wall and formed to correspond to the U-shaped contour of natural teeth as arranged on maxillae or on a mandible;
   a1) casting a liquid elastomer into a first bottom portion of the first cavity;
   a2) curing the liquid elastomer contained in the first cavity into a solid U-shaped elastomeric cushion, and removing the cushion from the first cavity;
   b) forming a plurality of socket cavities in the block of denture base material, the socket cavities extending downwardly from the bottom wall into the denture base material;
   c) casting a first fluid artificial tooth material into the plurality of socket cavities and into a portion of the first cavity, thereby filling the socket cavities and forming a top fluid surface in the first cavity;
   d) applying pressure to the first fluid artificial tooth material contained in the portion of the first cavity and the socket cavities; and
   e) causing the first fluid artificial tooth material to solidify into a first solid artificial tooth material while applying pressure to the first fluid artificial tooth material.

2. The method of claim 1, wherein the causing the first fluid artificial tooth material to solidify into a first solid artificial tooth material includes heating the first fluid artificial tooth material.

3. The method of claim 2, wherein heating the first fluid artificial tooth material is accomplished by heating a bottom of the block of denture base material, and causing heat transfer from the bottom of the block of denture base material into the first fluid artificial tooth material.

4. The method of claim 1, further comprising inserting the U-shaped elastomeric cushion into the first cavity after casting the first fluid artificial tooth material, and contacting the cushion with the top fluid surface of the first fluid artificial tooth material.

5. The method of claim 4, further comprising contacting a pressure element with the U-shaped elastomeric cushion and applying pressure to the cushion, thereby applying the pressure to the first fluid artificial tooth material contained in a second bottom portion of the first cavity and the socket cavities.

6. The method of claim 1, wherein the first fluid artificial tooth material is a methylmethacrylate powder and liquid mixture.

7. The method of claim 6, wherein the methylmethacrylate powder is comprised of methylmethacrylate monomers and polymers, and wherein the liquid mixture is caused to solidify into solid methylmethacrylate polymer.

* * * * *